United States Patent
Lloyd et al.

(10) Patent No.: US 9,320,569 B2
(45) Date of Patent: Apr. 26, 2016

(54) SYSTEMS AND METHODS FOR IMPLANT DISTANCE MEASUREMENT

(75) Inventors: Charles Frederick Lloyd, Reading, MA (US); Jon Thomas Lea, Hampstead, NH (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1484 days.

(21) Appl. No.: 11/559,727

(22) Filed: Nov. 14, 2006

(65) Prior Publication Data

US 2008/0114267 A1    May 15, 2008

(51) Int. Cl.
*A61B 19/00* (2006.01)
*A61B 17/70* (2006.01)

(52) U.S. Cl.
CPC .............. *A61B 19/5244* (2013.01); *A61B 19/52* (2013.01); *A61B 17/7001* (2013.01); *A61B 19/56* (2013.01); *A61B 2019/461* (2013.01); *A61B 2019/467* (2013.01); *A61B 2019/502* (2013.01); *A61B 2019/504* (2013.01); *A61B 2019/507* (2013.01); *A61B 2019/5238* (2013.01); *A61B 2019/5251* (2013.01); *A61B 2019/562* (2013.01); *A61B 2019/564* (2013.01)

(58) Field of Classification Search
CPC .............. A61B 19/5244; A61B 19/56; A61B 2019/461; A61B 2019/467; A61B 2019/504; A61B 2019/507; A61B 2019/562; A61B 2019/564
USPC .......................... 600/300, 411, 587, 407, 424
See application file for complete search history.

(56) References Cited

U.S. PATENT DOCUMENTS

| | | | | |
|---|---|---|---|---|
| 5,676,673 | A * | 10/1997 | Ferre et al. | 606/130 |
| 5,829,444 | A | 11/1998 | Ferre et al. | |
| 6,019,725 | A * | 2/2000 | Vesely et al. | 600/447 |
| 6,920,347 | B2 * | 7/2005 | Simon et al. | 600/424 |
| 7,107,091 | B2 | 9/2006 | Jutras et al. | |
| 7,195,632 | B2 | 3/2007 | Biedermann et al. | |
| 8,114,085 | B2 | 2/2012 | von Jako | |

(Continued)

FOREIGN PATENT DOCUMENTS

| | | |
|---|---|---|
| EP | 1534164 B1 | 11/2006 |
| EP | 1408859 B1 | 2/2008 |
| EP | 1267741 B1 | 8/2011 |
| JP | 2003-245289 A | 9/2003 |
| JP | 2004-521718 A | 7/2004 |

(Continued)

OTHER PUBLICATIONS

Japanese Office Action, application No. 2007-291480, Jul. 17, 2012 (4 pages).

*Primary Examiner* — Devin Henson
(74) *Attorney, Agent, or Firm* — McAndrews, Held & Malloy, Ltd.; William Baxter

(57) ABSTRACT

Certain embodiments of the present invention provide systems and methods for implant distance measurement. Certain embodiments of a method provide determining a tool trajectory, comparing the trajectory to one or more measured distances stored in memory to identify a requested distance measurement, and indicating the requested distance measurement to a user based on a matched trajectory. Certain embodiments of a system provide a processor configured to determine a tool trajectory with respect to a region of interest. The processor compares the trajectory to one or more measured distances between implants stored in memory to identify a requested distance measurement. The system also includes a display configured to display an image including the implants and the requested distance measurement to a user.

18 Claims, 6 Drawing Sheets

(56) References Cited

U.S. PATENT DOCUMENTS

| | | |
|---|---|---|
| 2003/0028091 A1 | 2/2003 | Simon et al. |
| 2004/0171924 A1* | 9/2004 | Mire ............... A61B 19/5244 600/407 |
| 2005/0085714 A1* | 4/2005 | Foley ............... A61B 17/1757 600/424 |
| 2007/0046677 A1* | 3/2007 | Hong et al. ............... 345/442 |

FOREIGN PATENT DOCUMENTS

| | | |
|---|---|---|
| JP | 2005-253727 A | 9/2005 |
| JP | 2005-533579 A | 11/2005 |
| JP | 2007-283101 A | 11/2007 |
| WO | 01/76497 A1 | 10/2001 |
| WO | 03/011156 A1 | 2/2003 |
| WO | 2004/010886 A1 | 2/2004 |

* cited by examiner

SYSTEMS AND METHODS FOR IMPLANT DISTANCE MEASUREMENT

BACKGROUND OF THE INVENTION

The present invention generally relates to image-guided surgery (or surgical navigation). In particular, the present invention relates to systems and methods for improved implant distance measurement.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Thus, medical navigation systems track the precise location of surgical instruments in relation to multidimensional images of a patient's anatomy. Additionally, medical navigation systems use visualization tools to provide the surgeon with co-registered views of these surgical instruments with the patient's anatomy. This functionality is typically provided by including components of the medical navigation system on a wheeled cart (or carts) that can be moved throughout the operating room.

Tracking systems may be ultrasound, inertial position, or electromagnetic tracking systems, for example. Electromagnetic tracking systems may employ coils as receivers and transmitters. Electromagnetic tracking systems may be configured in sets of three transmitter coils and three receiver coils, such as an industry-standard coil architecture (ISCA) configuration. Electromagnetic tracking systems may also be configured with a single transmitter coil used with an array of receiver coils or an array of transmitter coils with a single receiver coil, for example. Magnetic fields generated by the transmitter coil(s) may be detected by the receiver coil(s). For obtained parameter measurements, position and orientation information may be determined for the transmitter and/or receiver coil(s).

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Several areas of surgery involve very precise planning and control for placement of an elongated probe or other article in tissue or bone that is internal or difficult to view directly. In particular, for brain surgery, stereotactic frames that define an entry point, probe angle and probe depth are used to access a site in the brain, generally in conjunction with previously compiled three-dimensional diagnostic images, such as magnetic resonance imaging (MRI), positron emission tomography (PET) or computed tomography (CT) scan images, which provide accurate tissue images. For placement of pedicle screws in the spine, where visual and fluoroscopic imaging directions may not capture an axial view to center a profile of an insertion path in bone, such systems have also been useful.

When used with existing CT, PET or MRI image sets, previously recorded diagnostic image sets define a three dimensional (3D) rectilinear coordinate system, either by virtue of their precision scan formation or by the spatial mathematics of their reconstruction algorithms. However, it may be desirable to correlate the available fluoroscopic views and anatomical features visible from the surface or in fluoroscopic images with features in the 3-D diagnostic images and with external coordinates of tools being employed. Correlation is often done by providing implanted fiducials and/or adding externally visible or trackable markers that may be imaged. Using a keyboard, mouse or other pointer, fiducials may be identified in the various images. Thus, common sets of coordinate registration points may be identified in the different images. The common sets of coordinate registration points may also be trackable in an automated way by an external coordinate measurement device, such as a suitably programmed off-the-shelf optical tracking assembly. Instead of imageable fiducials, which may for example be imaged in both fluoroscopic and MRI or CT images, such systems may also operate to a large extent with simple optical tracking of the surgical tool and may employ an initialization protocol wherein a surgeon touches or points at a number of bony prominences or other recognizable anatomic features in order to define external coordinates in relation to a patient anatomy and to initiate software tracking of the anatomic features.

Generally, image-guided surgery systems operate with an image display which is positioned in a surgeon's field of view and which displays a few panels such as a selected MRI image and several x-ray or fluoroscopic views taken from different angles. Three-dimensional diagnostic images typically have a spatial resolution that is both rectilinear and accurate to within a very small tolerance, such as to within one millimeter or less. By contrast, fluoroscopic views may be distorted. The fluoroscopic views are shadowgraphic in that they represent the density of all tissue through which the conical x-ray beam has passed. In tool navigation systems, the display visible to the surgeon may show an image of a surgical tool, biopsy instrument, pedicle screw, probe or other device projected onto a fluoroscopic image, so that the surgeon may visualize the orientation of the surgical instrument in relation to the imaged patient anatomy. An appropriate reconstructed CT or MRI image, which may correspond to the tracked coordinates of the probe tip, may also be displayed.

Among the systems which have been proposed for implementing such displays, many rely on closely tracking the position and orientation of the surgical instrument in external coordinates. The various sets of coordinates may be defined by robotic mechanical links and encoders, or more usually, are defined by a fixed patient support, two or more receivers such as video cameras which may be fixed to the support, and a plurality of signaling elements attached to a guide or frame on the surgical instrument that enable the position and orientation of the tool with respect to the patient support and camera frame to be automatically determined by triangulation, so that various transformations between respective coordinates may be computed. Three-dimensional tracking systems employing two video cameras and a plurality of emitters or other position signaling elements have long been commercially available and are readily adapted to such operating room systems. Similar systems may also determine external position coordinates using commercially available acoustic ranging systems in which three or more acoustic emitters are actuated and their sounds detected at plural receivers to determine their relative distances from the detecting assemblies, and thus define by simple triangulation the position and orientation of the frames or supports on which the emitters are mounted. When tracked fiducials appear in the diagnostic images, it is possible to define a transformation between operating room coordinates and the coordinates of the image.

More recently, a number of systems have been proposed in which the accuracy of the 3D diagnostic data image sets is exploited to enhance accuracy of operating room images, by matching these 3D images to patterns appearing in intraoperative fluoroscope images. These systems may use tracking and matching edge profiles of bones, morphologically deforming one image onto another to determine a coordinate transform, or other correlation process. The procedure of correlating the lesser quality and non-planar fluoroscopic images with planes in the 3D image data sets may be time-consuming. In techniques that use fiducials or added markers, a surgeon may follow a lengthy initialization protocol or a slow and computationally intensive procedure to identify and correlate markers between various sets of images. All of these factors have affected the speed and utility of intraoperative image guidance or navigation systems.

Correlation of patient anatomy or intraoperative fluoroscopic images with precompiled 3D diagnostic image data sets may also be complicated by intervening movement of the imaged structures, particularly soft tissue structures, between the times of original imaging and the intraoperative procedure. Thus, transformations between three or more coordinate systems for two sets of images and the physical coordinates in the operating room may involve a large number of registration points to provide an effective correlation. For spinal tracking to position pedicle screws, the tracking assembly may be initialized on ten or more points on a single vertebra to achieve suitable accuracy. In cases where a growing tumor or evolving condition actually changes the tissue dimension or position between imaging sessions, further confounding factors may appear.

When the purpose of image guided tracking is to define an operation on a rigid or bony structure near the surface, as is the case in placing pedicle screws in the spine, the registration may alternatively be effected without ongoing reference to tracking images, by using a computer modeling procedure in which a tool tip is touched to and initialized on each of several bony prominences to establish their coordinates and disposition, after which movement of the spine as a whole is modeled by optically initially registering and then tracking the tool in relation to the position of those prominences, while mechanically modeling a virtual representation of the spine with a tracking element or frame attached to the spine. Such a procedure dispenses with the time-consuming and computationally intensive correlation of different image sets from different sources, and, by substituting optical tracking of points, may eliminate or reduce the number of x-ray exposures used to effectively determine the tool position in relation to the patient anatomy with the reasonable degree of precision.

However, each of the foregoing approaches, correlating high quality image data sets with more distorted shadow-graphic projection images and using tracking data to show tool position, or fixing a finite set of points on a dynamic anatomical model on which extrinsically detected tool coordinates are superimposed, results in a process whereby machine calculations produce either a synthetic image or select an existing data base diagnostic plane to guide the surgeon in relation to current tool position. While various jigs and proprietary subassemblies have been devised to make each individual coordinate sensing or image handling system easier to use or reasonably reliable, the field remains unnecessarily complex. Not only do systems often use correlation of diverse sets of images and extensive point-by-point initialization of the operating, tracking and image space coordinates or features, but systems are subject to constraints due to the proprietary restrictions of diverse hardware manufacturers, the physical limitations imposed by tracking systems and the complex programming task of interfacing with many different image sources in addition to determining their scale, orientation, and relationship to other images and coordinates of the system.

Several proposals have been made that fluoroscope images be corrected to enhance their accuracy. This is a complex undertaking, since the nature of the fluoroscope's 3D to 2D projective imaging results in loss of a great deal of information in each shot, so the reverse transformation is highly underdetermined. Changes in imaging parameters due to camera and source position and orientation that occur with each shot further complicate the problem. This area has been addressed to some extent by one manufacturer which has provided a more rigid and isocentric C-arm structure. The added positional precision of that imaging system offers the prospect that, by taking a large set of fluoroscopic shots of an immobilized patient composed under determined conditions, one may be able to undertake some form of planar image reconstruction. However, this appears to be computationally very expensive, and the current state of the art suggests that while it may be possible to produce corrected fluoroscopic image data sets with somewhat less costly equipment than that used for conventional CT imaging, intra-operative fluoroscopic image guidance will continue to involve access to MRI, PET or CT data sets, and to rely on extensive surgical input and set-up for tracking systems that allow position or image correlations to be performed.

Thus, it remains highly desirable to utilize simple, low-dose and low cost fluoroscope images for surgical guidance, yet also to achieve enhanced accuracy for critical tool positioning.

During a procedure, a spinal surgeon must maintain a precise sense of complex 3D anatomical relationships. Fluoroscopy is conventionally used intraoperatively to facilitate visualization of an anatomy (e.g., the pedicle) and placement of tools or implants (e.g., a guide wire or a pedicle screw). While fluoroscopy is useful, it is currently limited to only 2D projections of a complex 3D structure. Furthermore, fluoroscopy is only feasible along axes about the transverse plane, with anteroposterior (AP) and mediolateral (ML) views being most common. In this case, a surgeon cognitively infers surgical placement along a superior/inferior axis (i.e., an axial view) based on interpretation of landmarks in the images and knowledge of the anatomy. These types of inferences may lead to varying degrees of inaccuracy when placing pedicle screws in the spine, for example.

Computed tomographic (CT) imaging yields 3D volumetric images specific to each patient. This set of images may be re-rendered from practically any view and is conventionally presented as a series of axial cross-sections. It is commonly used preoperatively to diagnose a condition and to plan a surgical strategy.

Image guided navigation has been in clinical use for spinal surgery, among other applications. Image guided applications typically employ 2D fluoroscopic images or 3D CT datasets. 3D-based systems require explicit registration of the dataset to the patient, usually accomplished by manual digitization (e.g., picking points) of the patient's anatomy. 2D-based systems are simpler to use since images are intrinsically registered by tracking the imaging device (e.g., a fluoroscope) relative to the patient.

Thus, a hybrid 2D/3D navigation system that incorporates the ease of use and real-time updates of a 2D system along with an easily registered 3D CT dataset would be highly desirable.

Registration is a process of correlating two coordinate systems, such as a patient image coordinate system and an electromagnetic tracking coordinate system. Several methods may be employed to register coordinates in imaging applications. "Known" or predefined objects are located in an image. A known object includes a sensor used by a tracking system. Once the sensor is located in the image, the sensor enables registration of the two coordinate systems.

U.S. Pat. No. 5,829,444 by Ferre et al., issued on Nov. 3, 1998, refers to a method of tracking and registration using a headset, for example. A patient wears a headset including radiopaque markers when scan images are recorded. Based on a predefined reference unit structure, the reference unit may then automatically locate portions of the reference unit on the scanned images, thereby identifying an orientation of the reference unit with respect to the scanned images. A field generator may be associated with the reference unit to generate a position characteristic field in an area. When a relative position of a field generator with respect to the reference unit is determined, the registration unit may then generate an appropriate mapping function. Tracked surfaces may then be located with respect to the stored images.

However, registration using a reference unit located on the patient and away from the fluoroscope camera introduces inaccuracies into coordinate registration due to distance between the reference unit and the fluoroscope. Additionally, the reference unit located on the patient is typically small or else the unit may interfere with image scanning. A smaller reference unit may produce less accurate positional measurements, and thus impact registration.

Typically, a reference frame used by a navigation system is registered to an anatomy prior to surgical navigation. Registration of the reference frame impacts accuracy of a navigated tool in relation to a displayed fluoroscopic image.

Currently, it is difficult for a surgeon or other clinician to see implanted devices during percutaneous procedures. For spinal fusion, rods are inserted into implanted screws. These rods need to be selected or cut to a specific size. Making measurements without direct access to the screws can be problematic and is prone to trial-and-error methods. While not done currently, these distance measurements can be made automatically if the screws are placed with navigation. A difficulty with this approach is finding a way to efficiently filter out the many combinations of measurements and focus on the critical few. This problem becomes worse as the numbers of screws increases for a spinal fusion with several levels.

Thus, there is a need for systems and methods for improved implant distance measurement.

BRIEF SUMMARY OF THE INVENTION

Certain embodiments of the present invention provide systems and methods for implant distance measurement.

Certain embodiments of a method provide determining a tool trajectory, comparing the trajectory to one or more measured distances stored in memory to identify a requested distance measurement, and indicating the requested distance measurement to a user based on a matched trajectory.

Certain embodiments of a system provide a processor configured to determine a tool trajectory. The processor compares the trajectory to one or more measured distances between implants stored in memory to identify a requested distance measurement. The system also includes a display configured to display an image including the implants and the requested distance measurement to a user.

Certain embodiments provide a computer-readable medium having a set of instructions for execution on a computer. The set of instructions includes a trajectory measurement routine for determining a tool trajectory. The trajectory routine compares the tool trajectory to one or more measured distances to identify a requested distance measurement. The set of instructions also includes a display routine for indicating the requested distance measurement to a user based on a matched trajectory.

Figure 1:
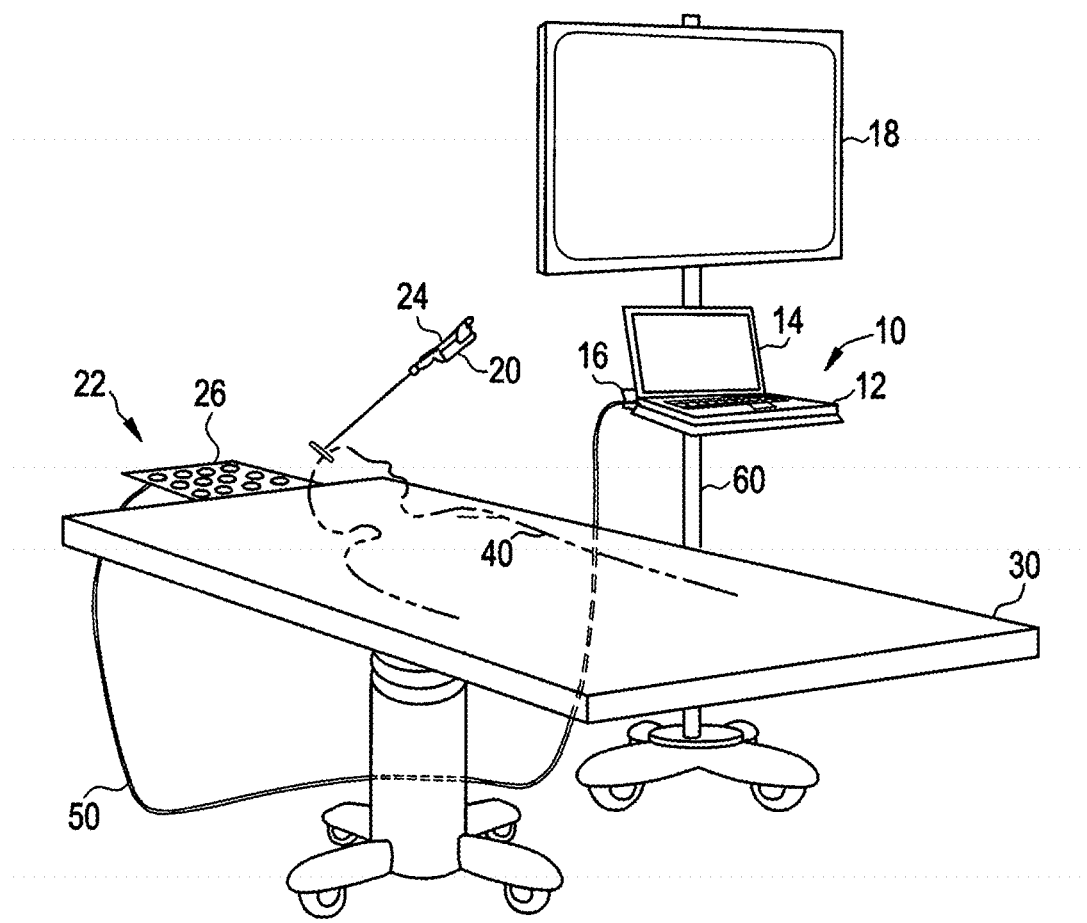
FIG. 1 illustrates a medical navigation system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Referring now to FIG. 1, a medical navigation system (e.g., a surgical navigation system), designated generally by reference numeral 10, is illustrated as including a portable computer 12, a display 14, and a navigation interface 16. The medical navigation system 10 is configured to operate with an electromagnetic field generator 20 and electromagnetic sensor 22 to determine the location of a device 24. Although the system 10 and/or other navigation or tracking system may be used in conjunction with a variety of tracking technologies, including electromagnetic, optical, ultrasound, inertial position and/or other tracking systems, for example, the system 10 is described below with respect to electromagnetic tracking for purposes of illustration only.

A table 30 is positioned near the electromagnetic sensor 22 to support a patient 40 during a surgical procedure. A cable 50 is provided for the transmission of data between, the electromagnetic sensor 22 and the medical navigation system 10. The medical navigation system 10 is mounted on a portable cart 60 with a second display 18 in the embodiment illustrated in FIG. 1.

The electromagnetic sensor 22 may be a printed circuit board, for example. Certain embodiments may include an electromagnetic sensor 22 comprising a printed circuit board receiver array 26 including a plurality of coils and coil pairs and electronics for digitizing magnetic field measurements detected in the printed circuit board receiver array 26. The magnetic field measurements can be used to calculate the position and orientation of the electromagnetic field generator 20 according to any suitable method or system. After the magnetic field measurements are digitized using electronics on the electromagnetic sensor 22, the digitized signals are transmitted to the navigation interface 16 through cable 50. As will be explained below in detail, the medical navigation system 10 is configured to calculate a location of the device 24 based on the received digitized signals.

The medical navigation system 10 described herein is capable of tracking many different types of devices during different procedures. Depending on the procedure, the device 24 may be a surgical instrument (e.g., an imaging catheter, a diagnostic catheter, a therapeutic catheter, a guidewire, a debrider, an aspirator, a handle, a guide, etc.), a surgical implant (e.g., an artificial disk, a bone screw, a shunt, a pedicle screw, a plate, an intramedullary rod, etc.), or some other device. Depending on the context of the usage of the medical navigation system 10, any number of suitable devices may be used.

Figure 2:
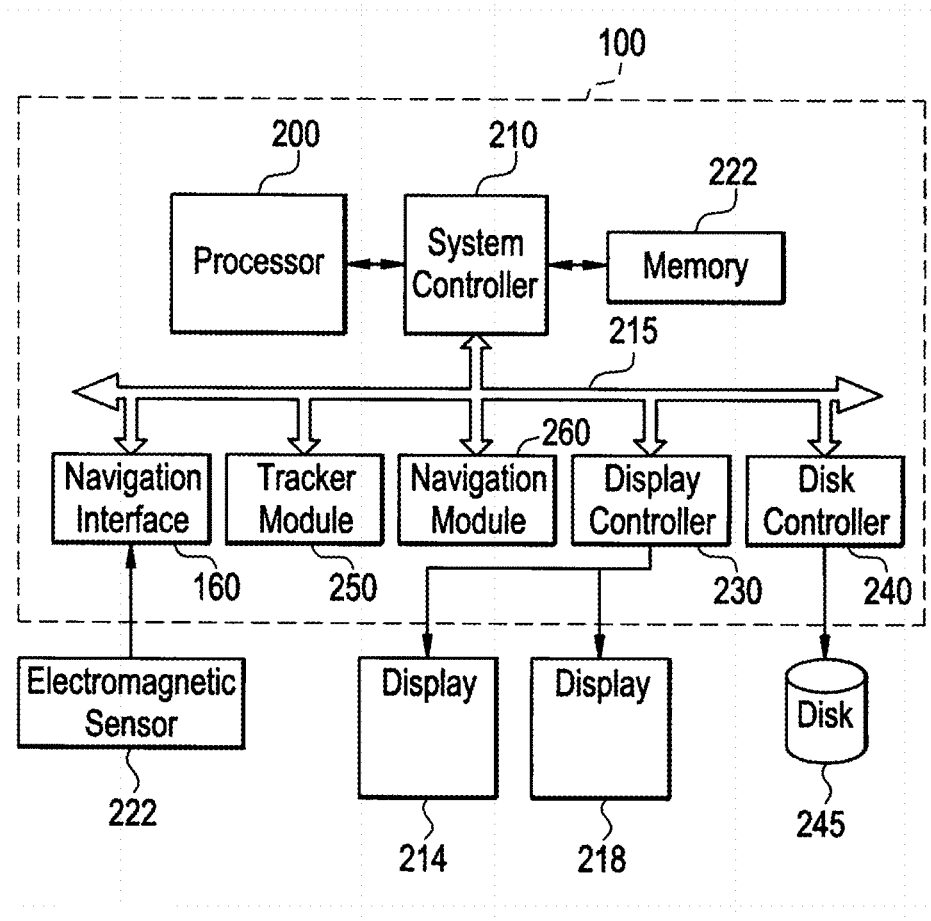
FIG. 2 illustrates a medical navigation system used in accordance with an embodiment of the present invention.

With regards to FIG. 2, an exemplary block diagram of the medical navigation system 100 is provided. The medical navigation system 100 is illustrated conceptually as a collection of modules, but may be implemented using any combination of dedicated hardware boards, digital signal processors, field programmable gate arrays, and processors. Alternatively, the modules may be implemented using an off-the-shelf computer with a single processor or multiple processors, with the functional operations distributed between the processors. As an example, it may be desirable to have a dedicated processor for position and orientation calculations as well as a dedicated processor for visualization operations. As a further option, the modules may be implemented using a hybrid configuration in which certain modular functions are performed using dedicated hardware, while the remaining modular functions are performed using an off-the-shelf computer. The operations of the modules may be controlled by a system controller 210.

The navigation interface 160 receives digitized signals from an electromagnetic sensor 222. In the embodiment illustrated in FIG. 1, the navigation interface 16 includes an Ethernet port. This port may be provided, for example, with an Ethernet network interface card or adapter. However, according to various alternate embodiments, the digitized signals may be transmitted from the electromagnetic sensor 222 to the navigation interface 160 using alternative wired or wireless communication protocols and interfaces.

The digitized signals received by the navigation interface 160 represent magnetic field information detected by an electromagnetic sensor 222. In the embodiment illustrated in FIG. 2, the navigation interface 160 transmits the digitized signals to the tracker module 250 over a local interface 215. The tracker module 250 calculates position and orientation information based on the received digitized signals. This position and orientation information provides a location of a device.

The tracker module 250 communicates the position and orientation information to the navigation module 260 over a local interface 215. As an example, this local interface 215 is a Peripheral Component Interconnect (PCI) bus. However, according to various alternate embodiments, equivalent bus technologies may be substituted without departing from the scope of the invention.

Upon receiving the position and orientation information, the navigation module 260 is used to register the location of the device to acquired patient data. In the embodiment illustrated in FIG. 2, the acquired patient data is stored on a disk 245. The acquired patient data may include computed tomography data, magnetic resonance data, positron emission tomography data, ultrasound data, X-ray data, or any other suitable data, as well as any combinations thereof. By way of example only, the disk 245 is a hard disk drive, but other suitable storage devices and/or memory may be used.

The acquired patient data is loaded into memory 220 from the disk 245. The navigation module 260 reads from memory 220 the acquired patient data. The navigation module 260 registers the location of the device to acquired patient data, and generates image data suitable to visualize the patient image data and a representation of the device. In the embodiment illustrated in FIG. 2, the image data is transmitted to a display controller 230 over a local interface 215. The display controller 230 is used to output the image data to two displays 214 and 218.

While two displays 214 and 218 are illustrated in the embodiment in FIG. 2, alternate embodiments may include various display configurations. Various display configurations may be used to improve operating room ergonomics, display different views, or display information to personnel at various locations. For example, as illustrated in FIG. 1, a first display 14 may be included on the medical navigation system 10, and a second display 18 that is larger than first display 14 is mounted on a portable cart 60. Alternatively, one or more of the displays 214 and 218 may be mounted on a surgical boom. The surgical boom may be ceiling-mounted, attachable to a surgical table, or mounted on a portable cart.

Figure 3:
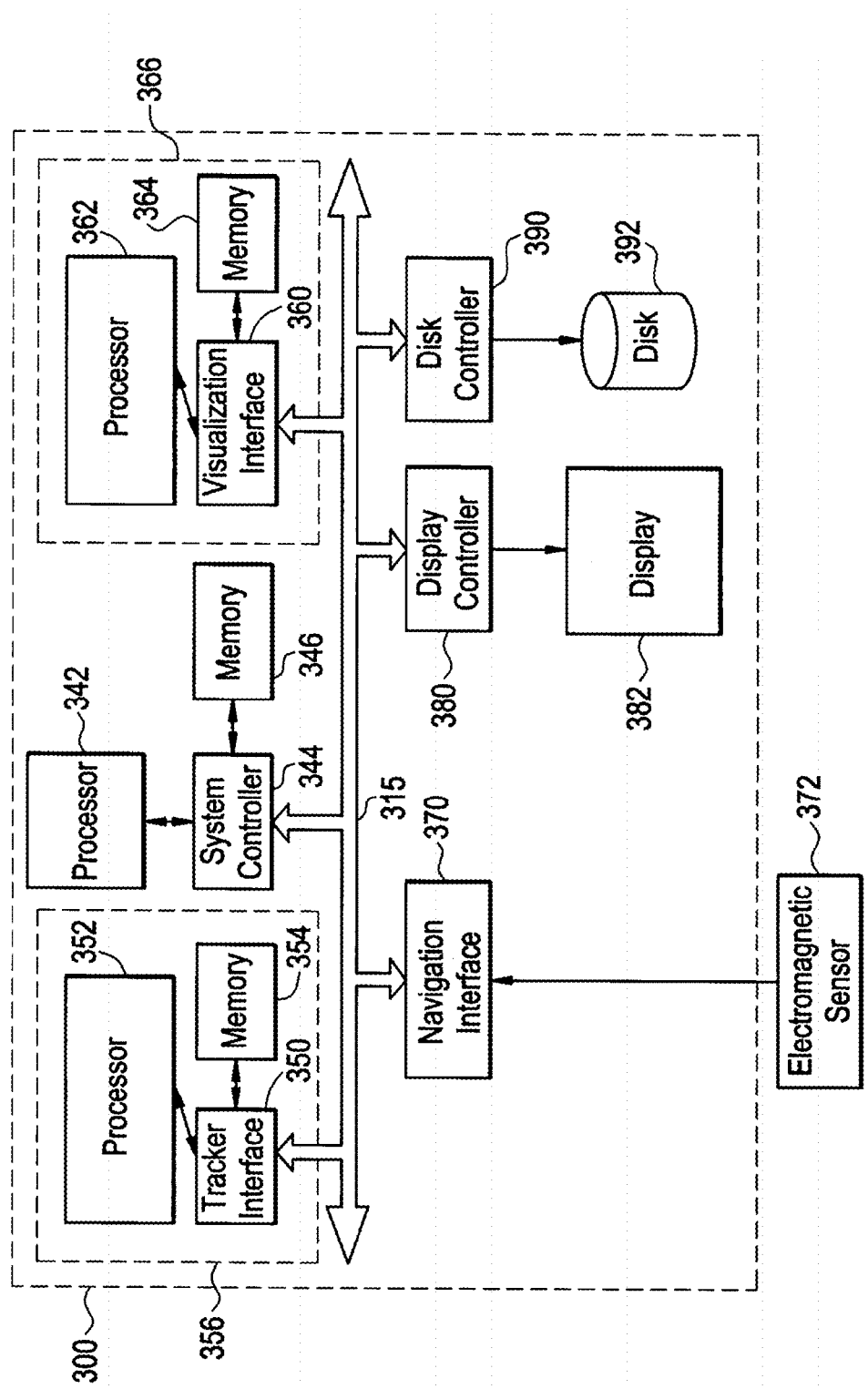
FIG. 3 illustrates a medical navigation system used in accordance with an embodiment of the present invention.

Referring now to FIG. 3, an alternative embodiment of a medical navigation system 300 is illustrated. The medical navigation system 300 comprises a portable computer with a relatively small footprint (e.g., approximately 1000 $cm^2$) and an integrated display 382. According to various alternate embodiments, any suitable smaller or larger footprint may be used.

The navigation interface 370 receives digitized signals from an electromagnetic sensor 372. In the embodiment illustrated in FIG. 3, the navigation interface 370 transmits the digitized signals to the tracker interface 350 over a local interface 315. In addition to the tracker interface 350, the tracker module 356 includes a processor 352 and memory 354 to calculate position and orientation information based on the received digitized signals.

The tracker interface 350 communicates the calculated position and orientation information to the visualization interface 360 over a local interface 315. In addition to the visualization interface 360, the navigation module 366 includes a processor 362 and memory 364 to register the location of the device to acquired patient data stored on a disk 392, and generates image data suitable to visualize the patient image data and a representation of the device.

The visualization interface 360 transmits the image data to a display controller 380 over a local interface 315. The display controller 380 is used to output the image data to display 382.

The medical navigation system 300 also includes a processor 342, system controller 344, and memory 346 that are used for additional computing applications such as scheduling, updating patient data, or other suitable applications. Performance of the medical navigation system 300 is improved by using a processor 342 for general computing applications, a processor 352 for position and orientation calculations, and a processor 362 dedicated to visualization operations. Notwithstanding the description of the embodiment of FIG. 3, alternative system architectures may be substituted without departing from the scope of the invention.

As will be described further below, certain embodiments of the present invention provide intraoperative navigation on 3D computed tomography (CT) datasets, such as an axial view, in addition to 2D fluoroscopic images. In certain embodiments, the CT dataset is registered to the patient intra-operatively via correlation to standard anteroposterior and lateral fluoroscopic images. Additional 2D images can be acquired and navigated as the procedure progresses without the need for re-registration of the CT dataset.

Certain embodiments provide tools enabling placement of multilevel procedures. Onscreen templating may be used to select implant length and size. The system may memorize the location of implants placed at multiple levels. A user may recall stored overlays for reference during placement of additional implants. Additionally, certain embodiments help eliminate trial-and-error fitting of components by making navigated measurements. In certain embodiments, annotations appear onscreen next to relevant anatomy and implants.

Certain embodiments utilize a correlation based registration algorithm to provide reliable registration. Standard anteroposterior (AP) and lateral (Lat) fluoroscopic images may be acquired. A vertebral level is selected, and the images are registered. The vertebral level selection is accomplished by pointing a navigated instrument at the actual anatomy, for example.

Certain embodiments of the system work in conjunction with a family of spine instruments and kits, such as a spine visualization instrument kit, spine surgical instrument kit, cervical instrument kit, navigation access needle, etc. These instruments facilitate the placement of a breadth of standard pedicle screws, for example. A library of screw geometries is used to represent these screws and facilitate an overlay of wireframe to fully shaded models. The overlays can be stored and recalled for each vertebral level.

In certain embodiments, recalled overlays can be displayed with several automatic measurements, including distance between multilevel pedicle screws, curvature between multilevel pedicle screws and annotations of level (e.g., Left L4 vertebra), for example. These measurements facilitate more precise selection of implant length and size. These measurements also help eliminate trial-and-error fitting of components.

Thus, certain embodiments aid a surgeon in locating anatomical structures anywhere on the human body during either open or percutaneous procedures. Certain embodiments may be used on lumbar and/or sacral vertebral levels, for example. Certain embodiments provide Digital Imaging and Communications in Medicine (DICOM) compliance and support for gantry tilt and/or variable slice spacing. Certain embodiments provide auto-windowing and centering with stored profiles. Certain embodiments provide a correlation-based 2D/3D registration algorithm and allow real-time multiplanar resection, for example.

Certain embodiments allow a user to store and recall navigated placements. Certain embodiments allow a user to determine a distance between multilevel pedicle screws and/or other implants/instruments. Certain embodiments allow a user to calculate interconnecting rod length and curvature, for example.

In certain embodiments, a user places screws and/or other implant(s) using navigation/tracking to obtain a position of the screws/other implants. While it is understood that a variety of implants may be used, the following description will be discussed in connection with a screw, such as a pedicle screw, for purposes of illustration only. Using navigation, the system remembers (e.g., stores in memory) locations of the placed screws. Based on position and orientation data gained from navigation, measurements of distances between the placed screws may be calculated.

The user then selects a desired view of the placed screws (e.g., an AP view), and the locations of the screws are shown with a marker or virtual screw overlay, for example. The user is able to choose from a variety of possible intra-screw measurements by aligning a trajectory of a pointer or other instrument with an axis along which the user is interesting in measuring. The trajectory may be determined by sampling the currently navigated (i.e., tracked) tool trajectory and/or by manipulating an on-screen widget, for example.

For example, to measure intra-screw distances for a spinal fusion, a user may select an AP view of the screws. Then, the user aligns a tool along a patient Superior-Inferior direction. To measure a cross-vertebral distance, the user aligns the current tool trajectory along a patient Right-Left direction. When the user aligns the tool trajectory with a measurement, that measurement is retrieved from memory and/or calculated based on tracking information and presented to the user. The distance measurement may be displayed in a text-based and/or graphical form to the user, for example.

Thus, a user may measure distances above the skin without an invasive procedure. Providing information through a user interface facilitates a surgeon's direct filtering of the information displayed using the physical analog of the navigated instrument. Additionally, the surgeon does not need to break the sterile field. Certain embodiments intuitively interact with the user to target desired information.

Although the systems and methods described herein may be used with a variety of implants, an example of a screw (and more specifically a pedicle screw) is used below for convenient purposes of illustration only. Such an example is not intended to limit the embodiments disclosed and encompassed herein to screw implants.

Figure 4:
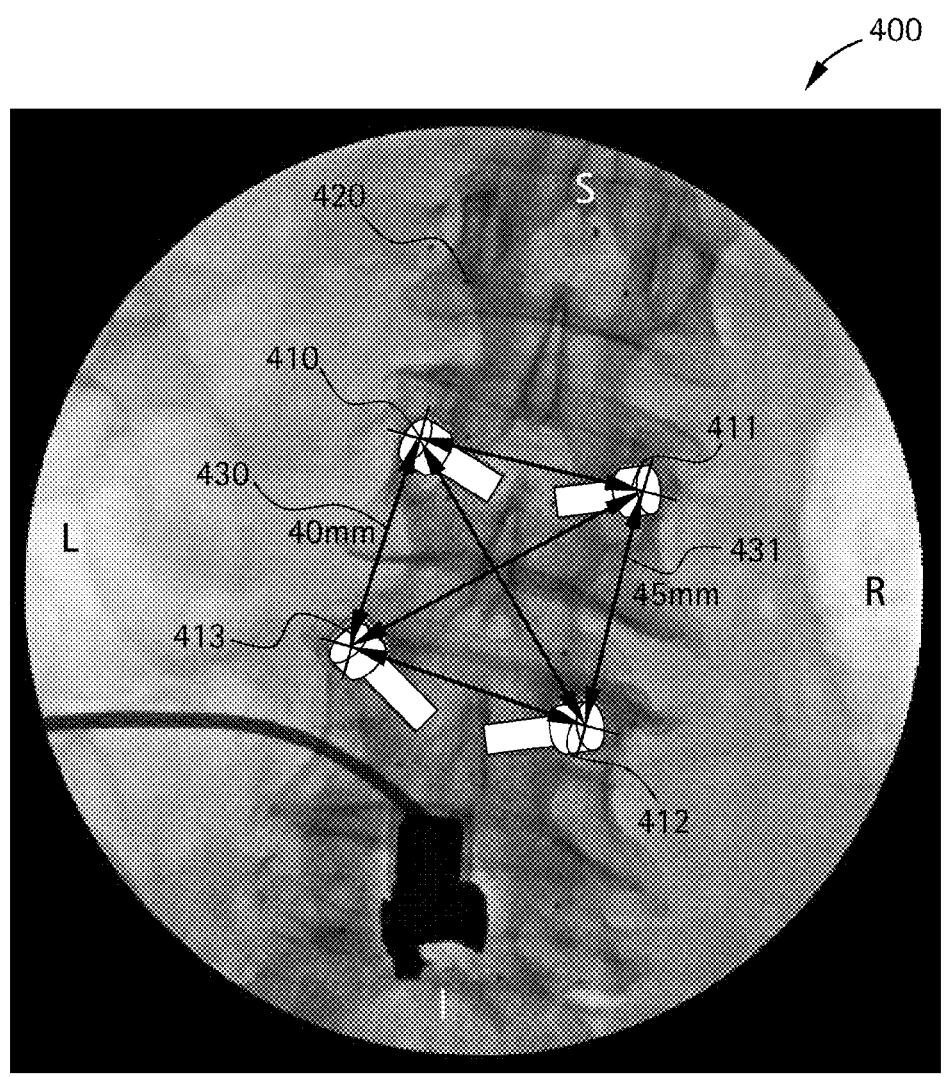
FIG. 4 illustrates an example of a user interface displaying an image with implant position and measurement information in accordance with an embodiment of the present invention.

As shown, for example, in FIG. 4, a plurality of screws 410-413 are placed in a plurality of vertebrae in a patient's spine 420. Positional measurements of the implanted screws may be taken automatically by a tracking system and/or in conjunction with a user initiation (e.g., by user trigger based on a button click, pressure on the tool, keyboard selection, mouse selection, etc.).

Rods may be inserted between the screws to facilitate a spinal fusion, for example. Rods are available in a variety of sizes and may be bent and/or cut to a variety of sizes and/or curvatures, for example. A user is provided with measurement data between the screws to aid in determining proper rod length and/or curvature, for example.

A user positions a navigated or tracked tool with respect to the image of the patient anatomy, such as the image of FIG. 4. When the tool is aligned or substantially aligned with a measurement, that measurement is displayed on the image and/or in conjunction with the image to provide feedback to the user. For example, if the user aligns the tool along trajectory 430, a measured distance of 40 mm is displayed on the image. If the user aligns the tool along trajectory 431, a measured distance of 45 mm is displayed on the image. Thus, through user interaction, pertinent information may be displayed for the user while non-relevant information is kept hidden.

In certain embodiments, a relevant measurement is identified as follows. A trajectory or path between screws and/or other implants is known based on tracking information. Additionally, a trajectory of the tool is known based on tracking information. The trajectory of the tool is compared to the measured path between the screws. If the angle between the paths is less than a certain threshold, for example, then that measurement is provided. The angle may be determined as a 3D angle and/or as a 2D angle (e.g., an angle in 3D space mapped onto a 2D plane). Furthermore, a comparison of a measured angle to a threshold angle may be a comparison of apparent angles. That is, the displayed image is viewed from a specific angle and appears flat on a display but could also be tilted into or out of the display. The comparison may account for other angles (e.g., looking at angles in three dimensions) when determining a relevant measurement to display.

Figure 5:
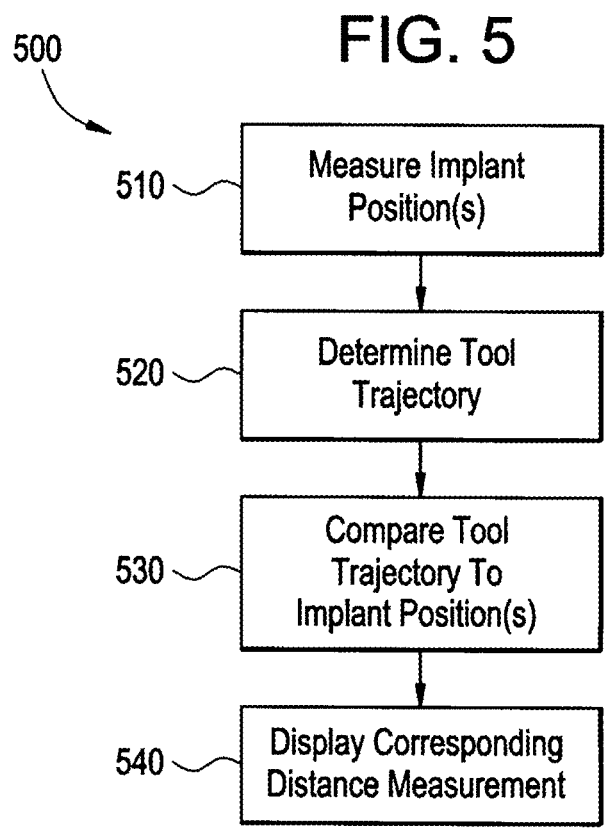
FIG. 5 illustrates a flowchart for a method for implant distance measurement used in accordance with an embodiment of the present invention.

FIG. 5 illustrates a flowchart for a method 500 for implant distance measurement used in accordance with an embodiment of the present invention. At step 510, implant positions are measured. For example, position and orientation information for a plurality of pedicle screws implanted in a patient spine is measured. Implant representation may be displayed on an image for user review. At step 520, tool trajectory is determined. For example, tool position and/or trajectory information is determined with respect to the imaging area.

At step 530, tool trajectory is compared to implant positions. For example, an angle between tool trajectory and implant position trajectory may be measured or locations may be otherwise compared in the image space to determine a corresponding implant distance. The angle may be examined in 2D and/or in 3D to determine a correlation, for example. At step 540, the corresponding distance measurement between implants is displayed to the user. For example, a path between two implants with a corresponding distance measurement may be graphically indicated on a displayed image. Alternatively and/or in addition, distance measurement data may be provided to a user aside from a displayed image, for example.

At step 540, tool trajectory may be adjusted to display different measurement information. As described above, an inter-implant distance may be displayed based on tool positioning with respect to the image area.

Additionally, in certain embodiments, distance measurement information may be used to provide one or more recommendations regarding rod selection, such as suggested rod length and/or curvature. For example, surgical procedures often involve fitting several interlocking components together. For example, pedicle screws are placed in adjacent vertebral levels and secured to one another by an interconnecting rod. The size of this rod is determined by the distance between the heads of the two pedicle screws. For example, a distance between pedicle screws in three adjacent vertebrae is determined for interconnecting rod measurement. Selection of the appropriate rod size is often accomplished by trial-and-error fitting and/or visual estimation. Navigation may be employed to provide measurement information instead and/or in addition.

Additionally, pedicle screw and/or other implant placement may be stored to aid in subsequent implant placement. For example, a placement location of a pedicle screw may be stored or otherwise maintained while placing additional screws at adjacent levels. Knowing prior placement at adjacent levels may help subsequent screws to be driven to like depths and angles. Thus, insertion of an interconnecting rod between the screws may be improved.

Thus, certain embodiments provide workflow enhancement for surgical navigation and measurement. For example, the distance between two pedicle screw heads is used to determine the size of the interconnecting rod. Navigation helps improve workflow to measure the distance rather than manual measurement via calipers and a sizing template. Additionally, navigated pedicle screws may be graphically rendered and represented as an overlay on an image for viewing by a clinician. The overlay helps maintain visualization of screw and/or other implant locations, for example.

Certain embodiments operate in conjunction with a 2D/3D hybrid navigation system incorporates real-time updating and ease of use of a 2D system along with an easily registered 3D CT dataset. Safety and precision of medical procedures may be enhanced with a 2D/3D navigation system. Use of a CT dataset along with 2D intraoperative imaging adds to visualization and understanding of an anatomy in an operating room. Such a system may have applicability in a variety of medical procedures, such as spinal procedures, cranial procedures and other clinical procedures. Spinal procedures may include posterolateral open and minimally invasive surgical (MIS) pedicle screws, posterior C1-C2 transarticular screw fixation, transoral odontoid fixation, cervical lateral mass plate screw fixation, anterior thoracic screw fixation, scoliosis, kyphosis, kyphoplasty, vertebroplasty, transforaminal lumbar interbody fusion (TLIF), artificial disks, burst fractures, excision of paraspinal neoplasms, etc.

Figure 6:
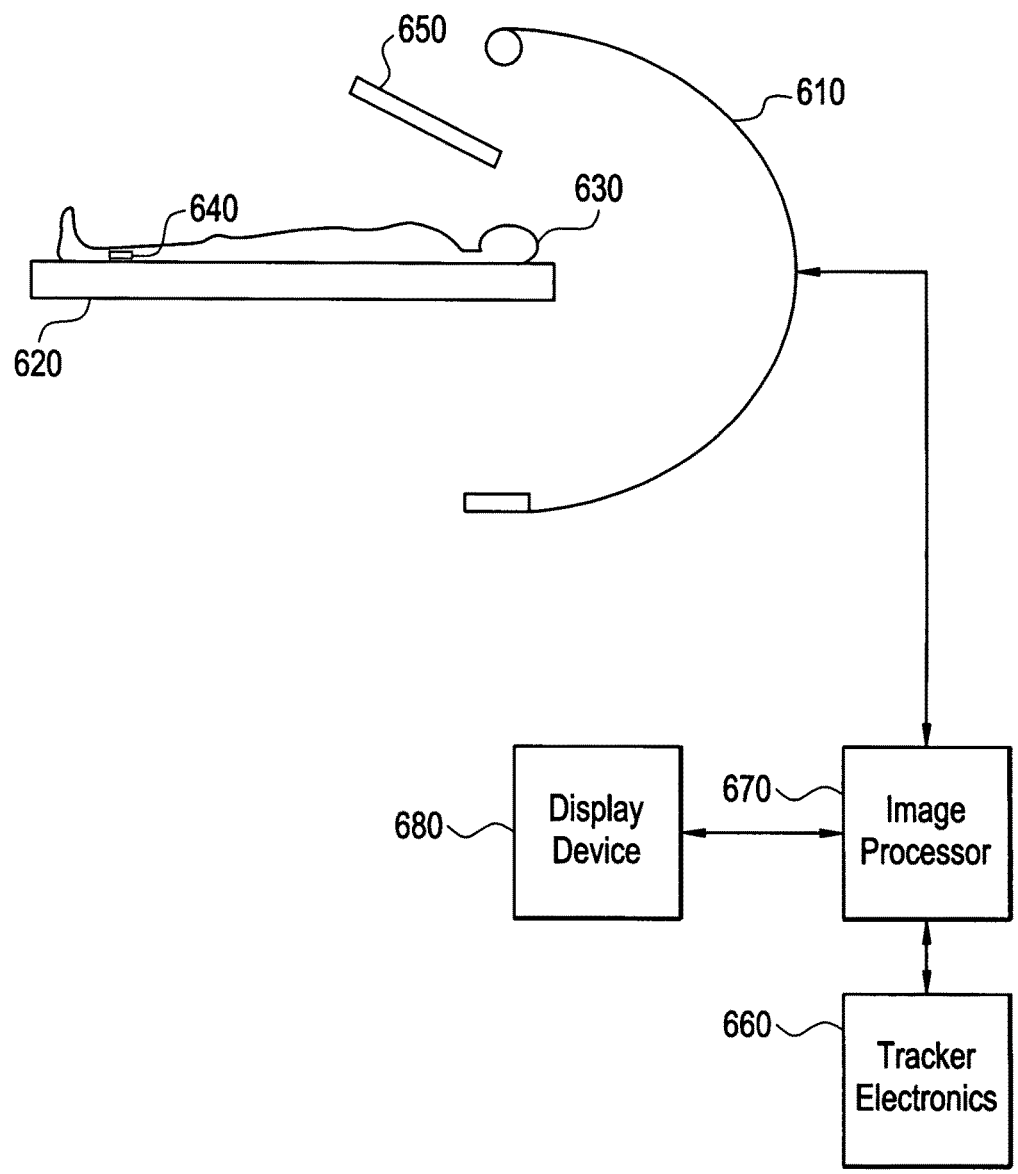
FIG. 6 illustrates an exemplary imaging and tracking system used in accordance with an embodiment of the present invention.

Alternatively and/or in addition, certain embodiments may be used in conjunction with an imaging and tracking system, such as the exemplary imaging and tracking system 600 illustrated in FIG. 6. System 600 includes an imaging device 610, a table 620, a patient 630, a tracking sensor 640, a medical device or implant 650, tracker electronics 660, an image processor 670, and a display device 680. Imaging device 610 is depicted as a C-arm useful for obtaining x-ray images of an anatomy of patient 630, but may be any imaging device 610 useful in a tracking system. Imaging device or modality 610 is in communication with image processor 670. Image processor 670 is in communication with tracker electronics 660 and display device 680. Tracker electronics 660 is in communication (not shown) with one or more of a tracking sensor attached to imaging modality 610, a tracking sensor attached to medical instrument 650 and sensor 640.

Sensor 640 is placed on patient to be used as a reference frame in a surgical procedure. For example, sensor 640 may be rigidly fixed to patient 630 in an area near an anatomy where patient 630 is to have an implant 650 inserted or an instrument 650 employed in a medical procedure. The instrument or implant 650 may also include a sensor, thereby allowing for the position and/or orientation of the implant or instrument 650 to be tracked relative to the sensor 640. Sensor 640 may include either a transmitting or receiving sensor, or include a transponder.

In operation, for example, imaging modality 610 obtains one or more images of a patient anatomy in the vicinity of sensor 640. Tracker electronics 660 may track the position and/or orientation of any one or more of imaging modality 610, sensor 640 and instrument 650 relative to each other and communicate such data to image processor 670.

Imaging modality 610 can communicate image signals of a patient's anatomy to the image processor 670. Image processor 670 may then combine one or more images of an anatomy with tracking data determined by tracker electronics 660 to create an image of the patient anatomy with one or more of sensor 640 and instrument 650 represented in the image. For example, the image may show the location of sensor 640 relative to the anatomy or a region of interest in the anatomy.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represents examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any medical navigation system. Certain features of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A method for implant distance measurement, said method comprising:

using a user interface to display a tool and one or more representations of distance, each representation of distance being associated with a distance measurement between two implants, each representation of distance being associated with a trajectory;

using a computer processor to determine a tool trajectory of the tool based on a location of the tool;

using the computer processor to compare said tool trajectory to the trajectories associated with the one or more representations of distance;

using the computer processor to identify a representation of distance that is associated with a trajectory that matches the tool trajectory, the matching trajectories indicating that the tool and the identified representation of distance are substantially aligned; and using the user interface to display the distance measurement between two implants that is associated with the identified representation of distance in response to the computer processor identifying the matching trajectories of the tool and the identified representation of distance.

2. The method of claim 1, wherein said tool trajectory is matched to the trajectory associated with the representation of distance based on a comparison of an angle between said tool trajectory and the trajectory associated with the representation of distance.

3. The method of claim 1, further comprising using the user interface to highlight the identified representation of distance.

4. The method of claim 1, further comprising recommending an interconnection component characteristic based on said identified representation of distance.

5. The method of claim 1, further comprising storing implant placement and identified representation of distance information for subsequent implant placement.

6. The method of claim 1, wherein said tool trajectory is determined based on tracking information for the tool.

7. The method of claim 1, wherein the distance between two implants associated with said one or more representations of distance are determined based on tracking information for the implants.

8. The method of claim 1, further comprising using the user interface to display one or more implants overlaid on an image with said identified representation of distance.

9. The method of claim 1, wherein said tool trajectory is matched to the trajectory associated with the representation of distance if an angle between said tool trajectory and the trajectory associated with the representation of distance is less than a threshold.

10. A non-transitory computer-readable medium having a set of instructions for execution on a computer, said set of instructions comprising:
   a first routine configured to display a tool and one or more representations of distance, each representation of distance being associated with a distance measurement between two implants, each representation of distance being associated with a trajectory;
   a second routine configured to determine a tool trajectory of the tool based on a location of the tool;
   a third routine configured to compare said tool trajectory to the trajectories associated with the one or more representations of distance;
   a fourth routine configured to identify a representation of distance that is associated with a trajectory that matches the tool trajectory, thereby determining that the tool and the identified representation of distance are substantially aligned; and
   a fifth routine configured to display the distance measurement between two implants that is associated with the identified representation of distance in response to the fourth routine identifying the matching trajectories of the tool and the identified representation of distance.

11. The medium and instructions of claim 10, wherein said tool trajectory is matched to the trajectory associated with the representation of distance based on a comparison of an angle between said tool trajectory and the trajectory associated with the representation of distance.

12. The medium and instructions of claim 10, further comprising a sixth routine configured to highlight the identified representation of distance.

13. The medium and instructions of claim 10, further comprising a sixth routine configured to recommend an interconnection component characteristic based on said identified representation of distance.

14. The medium and instructions of claim 10, further comprising a sixth routine configured to storing implant placement and identified representation of distance information for subsequent implant placement.

15. The medium and instructions of claim 10, wherein said tool trajectory is determined based on tracking information for the tool.

16. The medium and instructions of claim 10, wherein the distance between two implants associated with said one or more representations of distance are determined based on tracking information for the implants.

17. The medium and instructions of claim 10, further comprising a sixth routine configured to display one or more implants overlaid on an image with said identified representation of distance.

18. The medium and instructions of claim 10, wherein said tool trajectory is matched to the trajectory associated with the representation of distance if an angle between said tool trajectory and the trajectory associated with the representation of distance is less than a threshold.

\* \* \* \* \*